(12) United States Patent
Na et al.

(10) Patent No.: US 11,285,188 B2
(45) Date of Patent: Mar. 29, 2022

(54) COMPOSITION FOR PREVENTING OR TREATING METABOLIC DISEASES CONTAINING ARTEMISIAE CAPILLARIS HERBA AND CITRUS UNSHIU PEEL COMPLEX EXTRACTS AS ACTIVE INGREDIENTS

(71) Applicant: Medicare Pharmaceuticals Inc., Jeollabuk-do (KR)

(72) Inventors: Do Hyun Na, Seoul (KR); Jin Hwan Jun, Goyang-si (KR); Kyung Pyo Kang, Goyang-si (KR)

(73) Assignee: Medicare Pharmaceuticals Inc., Jeollabuk-do (KR)

( * ) Notice: Subject to any disclaimer, the term of this patent is extended or adjusted under 35 U.S.C. 154(b) by 223 days.

(21) Appl. No.: 16/676,937

(22) Filed: Nov. 7, 2019

(65) Prior Publication Data

US 2020/0171113 A1     Jun. 4, 2020

(30) Foreign Application Priority Data

Nov. 30, 2018 (KR) .......... 10-2018-0152162

(51) Int. Cl.
| | |
|---|---|
| *A61K 36/282* | (2006.01) |
| *A61K 9/00* | (2006.01) |
| *A61K 9/16* | (2006.01) |
| *A61K 9/20* | (2006.01) |
| *A61K 36/752* | (2006.01) |

(52) U.S. Cl.
CPC .......... *A61K 36/282* (2013.01); *A61K 9/0056* (2013.01); *A61K 9/0095* (2013.01); *A61K 9/1623* (2013.01); *A61K 9/1652* (2013.01); *A61K 9/1664* (2013.01); *A61K 9/2013* (2013.01); *A61K 9/2018* (2013.01); *A61K 9/2059* (2013.01); *A61K 36/752* (2013.01); *A61K 2236/333* (2013.01)

(58) Field of Classification Search
CPC .............. A61K 2300/00; A61K 36/282; A61K 36/752; A61K 2236/333; A61K 9/0056; A61K 9/0095; A61K 9/1623; A61K 9/1652; A61K 9/1664; A61K 9/2013; A61K 9/2018; A61K 9/2059; A61K 9/4858; A23V 2002/00; A23V 2200/3262; A23V 2250/21; A23V 2200/328; A23L 33/105; A23L 7/00; A23G 9/42; A61P 3/00
See application file for complete search history.

(56) References Cited

U.S. PATENT DOCUMENTS

| | | | |
|---|---|---|---|
| 2012/0251567 A1* | 10/2012 | Nam .............. | A61K 36/48 424/195.15 |
| 2016/0220622 A1* | 8/2016 | Park ................ | A61P 1/16 |

FOREIGN PATENT DOCUMENTS

| | | |
|---|---|---|
| KR | 10-0786122 B1 | 12/2007 |
| KR | 10-2008-0090163 A | 10/2008 |

OTHER PUBLICATIONS

"Report of the Formal Meeting of Member States to conclude the work on the comprehensive global monitoring framework, including indicators, and a set of voluntary global targets for the prevention and control of noncommunicable diseases", World Health Organization, A/NCD/2, Nov. 2012, pp. 1-6.
"Dyslipidemia Medical Care Guidelines (3rd Edition)", The Korean Society of Lipid and Atherosclerosis, 2015, 163 pages.
Geum-Hee Hwang, et al., "A Study of Hyperlipidemia in Koreans—I. Specially Related to Physical Characteristics and It's Risk Factors for Hypercholesterolemia—", Korean J. Food & Nutr., 1999, pp. 279-289, vol. 12, No. 3.
Jung-Ran Noh, et al., "Scoparone inhibits adipocyte differentiation through down-regulation of peroxisome proliferators-activated receptor γ in 3T3-L1 preadipocytes", Food Chemistry, 2013, pp. 723-730 , vol. 141.
Dong Wook Lim, et al., "Anti-Obesity Effect of Artemisia capillaris Extracts in High-Fat Diet-Induced Obese Rats", Molecules, 2013, pp. 9241-9252, vol. 18.
Hyun Kyun Jo, et al., "Ethanol Extracts of Citrus Peel Inhibits Adipogenesis through AMPK Signaling Pathway in 3T3-L1 Preadipocytes", Journal of Life Science, 2015, pp. 285-292, vol. 25, No. 3.
Notice of Allowance issued from Korean Patent Application No. 10-2018-0152162 dated Jul. 10, 2019.

\* cited by examiner

*Primary Examiner* — Aaron J Kosar
(74) *Attorney, Agent, or Firm* — Sughrue Mion, PLLC

(57) ABSTRACT

The present disclosure relates to a composition for preventing or treating metabolic diseases, the composition containing *Artemisiae capillaris* Herba and *Citrus unshiu* Peel complex extracts as active ingredients. Specifically, in the *Artemisiae capillaris* Herba and *Citrus unshiu* Peel complex extracts according to the present disclosure, the content of ingredients useful for prevention of metabolic diseases including obesity is much higher than in extracts obtained only from *Artemisiae capillaris* Herba. In addition, when a high-fat diet mouse model is administered the complex extracts, the levels of total cholesterol, LDL, and triglycerides in the blood are reduced. Accordingly, the complex extracts of the present disclosure may be used as a composition or functional material for preventing or treating metabolic diseases including obesity, hyperlipidemia, and hypercholesterolemia.

4 Claims, No Drawings

COMPOSITION FOR PREVENTING OR TREATING METABOLIC DISEASES CONTAINING ARTEMISIAE CAPILLARIS HERBA AND CITRUS UNSHIU PEEL COMPLEX EXTRACTS AS ACTIVE INGREDIENTS

CROSS-REFERENCE TO RELATED APPLICATION

This application claims priority to Korean Patent Application No. 10-2018-0152162, filed on Nov. 30, 2018 in the Korean Intellectual Property Office, the disclosure of which is incorporated herein by reference.

BACKGROUND OF THE DISCLOSURE

Field of the Disclosure

The present disclosure relates to a composition for preventing or treating metabolic diseases, the composition containing *Artemisiae capillaris* Herba and *Citrus unshiu* Peel complex extracts as active ingredients, and more particularly, to a pharmaceutical composition and a functional health food for preventing or alleviating metabolic diseases, each containing *Artemisiae capillaris* Herba and *Citrus unshiu* Peel complex extracts as active ingredients.

Description of the Related Art

Metabolic diseases refer to diseases caused by imbalance of sugars, lipids, proteins, vitamins, minerals, or water. Thereamong, lipid-related metabolic diseases are caused by excessive lipid accumulation in vivo, and include obesity, diabetes, hyperlipidemia, hypercholesterolemia, and the like. In addition, lipid-related metabolic diseases are closely associated with westernization of eating habits and lack of exercise.

In recent years, with improvement in living standards associated with industrialization, dietary patterns of eating high calorie foods such as meat have become prevalent. In addition to these dietary habits, lack of exercise led to a sharp increase in the obese population. Obesity refers to a condition wherein excess fat is accumulated in the body, and is caused by the imbalance between energy accumulation and energy consumption due to excessive food intake and lack of exercise. In particular, obesity is accompanied by metabolic disorders such as hypertension, hyperlipidemia, low HDL cholesterol, impaired glucose tolerance, or type 2 diabetes, which can be a fatal risk to health.

In addition, hypercholesterolemia characterized by a high cholesterol level in the body is a risk factor that causes cardio-cerebrovascular diseases, as described by the World Health Organization (WHO), and is known to be caused by dietary factors such as excessive intake of saturated fatty acids or cholesterol, overeating, and drinking.

Hyperlipidemia, the most important independent cause of atherosclerosis, refers to a condition wherein the amount of cholesterol or triglycerides in the blood is increased above normal levels. Hyperlipidemia is closely associated with westernization of lifestyle, excessive calorie intake, increased intake of animal fats, increase in an average body weight, lack of exercise, increased stress, increased life expectancy, and increase in the elderly population. These factors are mainly related to dietary habits and weight control. In particular, obesity is known to cause hyperlipidemia by causing abnormalities in cholesterol and lipoprotein metabolism. Overweight or obese people have been reported to have higher levels of plasma cholesterol or triglycerides than those of normal people.

In a complex modern society faced with problems such as deterioration of living environment caused by environmental pollution, increased mental stress, and lack of exercise, interest in health promotion is rapidly increasing. In particular, modern people who are unable to exercise due to busy daily life, fatigue, and the like are interested in eating a variety of functional foods as an alternative to exercise. However, misuse of functional foods or excessive exercise may cause fatal side effects. Accordingly, in recent years, need for development of functional foods using natural products with guaranteed safety, such as plant extracts, is increasing.

Therefore, the present inventors have tried to develop a material that is guaranteed in terms of food safety and is capable of treating or preventing metabolic diseases including hyperlipidemia, hypercholesterolemia, and the like caused by obesity. As a result, the inventors found that the content of ingredients useful for prevention of metabolic diseases including obesity was remarkably high in complex extracts prepared by mixing *Artemisiae capillaris* Herba and *Citrus unshiu* Peel, and confirmed that the levels of total cholesterol, LDL, and triglycerides in the blood were reduced when the complex extracts were orally administered in a high-fat diet mouse model. Thus, the present inventors completed the present invention by revealing that the complex extracts of the present disclosure can be used as a composition or functional material for preventing or treating metabolic diseases including obesity, hyperlipidemia, and hypercholesterolemia.

RELATED ART DOCUMENTS

Patent Documents (Patent Document 1) Korean Patent Application Publication No. 10-2008-0090163

Non-Patent Documents (Non-Patent Document 1) WHO. Report of the Formal Meeting of Member States to Conclude the Work on the Comprehensive Global Monitoring Framework. 2012.

(Non-Patent Document 2) Dyslipidemia Medical Care Guidelines (3rd Edition). The Korean Society of Lipid and Atherosclerosis. 2015.

(Non-Patent Document 3) Hwang G H and Huh Y R. A Study of Hyperlipidemia in Koreans: I. Specially Related to Physical Characteristics and It's Risk Factors for Hypercholesterolemia. Korean J Food Nutr 1999; 12(3): 279-89.

(Non-Patent Document 4) Jung-Ran Noh, Yong-Hoon Kim, Jung Hwan Hwang, Gil-Tae Gang, Seung-Hoon Yeo, Kyoung-Shim Kim, Won-Keun Oh, Sun-Yung Ly, In-Kyu Lee, and Chul-Ho Lee. Scoparone Inhibits Adipocyte Differentiation through Down-regulation of Peroxisome Proliferators-activated Receptor y in 3T3-L1 Preadipocytes. Food Chemistry 141 (2013) 723-730.

SUMMARY OF THE DISCLOSURE

Therefore, the present disclosure has been made in view of the above problems, and it is an object of the present disclosure to provide a pharmaceutical composition for preventing or treating metabolic diseases, the pharmaceutical composition containing *Artemisiae capillaris* Herba and *Citrus unshiu* Peel complex extracts as active ingredients.

It is another object of the present disclosure to provide a functional health food for preventing or alleviating metabolic diseases, the functional health food containing *Artemisiae capillaris* Herba and *Citrus unshiu* Peel complex extracts as active ingredients.

In accordance with one aspect of the present disclosure, provided is a pharmaceutical composition for preventing or treating metabolic diseases, the pharmaceutical composition containing *Artemisiae capillaris* Herba and *Citrus unshiu* Peel complex extracts as active ingredients.

In accordance with another aspect of the present disclosure, provided is a functional health food for preventing or alleviating metabolic diseases, the functional health food containing *Artemisiae capillaris* Herba and *Citrus unshiu* Peel complex extracts as active ingredients.

DETAILED DESCRIPTION OF THE DISCLOSURE

Hereinafter, the present disclosure will be described in detail.

The present disclosure provides a pharmaceutical composition for preventing or treating metabolic diseases, the pharmaceutical composition containing *Artemisiae capillaris* Herba and *Citrus unshiu* Peel complex extracts as active ingredients.

According to the present disclosure, the *Artemisiae capillaris* Herba and *Citrus unshiu* Peel complex extracts used as active ingredients are preferably prepared by a method including the following steps, but the present disclosure is not limited thereto:

Step 1 of performing extraction by adding an extraction solvent to *Artemisiae capillaris* Herba and *Citrus unshiu* Peel; and Step 2 of filtering the extracts obtained in Step 1.

In Step 1, cultivated or commercially available *Artemisiae capillaris* Herba and *Citrus unshiu* Peel may be used without limitation.

In Step 1, water, an alcohol, or a mixture thereof is preferably used as the extraction solvent. The alcohol is preferably a lower alcohol having 1 to 2 carbon atoms, and the lower alcohol is preferably ethanol or methanol. The extraction method preferably includes ultrasonic extraction, shaking extraction, Soxhlet extraction, or reflux extraction, without being limited thereto. In performing the extraction, the extraction solvent is preferably added to the completely dried *Artemisiae capillaris* Herba and *Citrus unshiu* Peel after washing in an amount of 1 to 15 times, more preferably 2 to 10 times, the amount of the *Artemisiae capillaris* Herba and *Citrus unshiu* Peel. In this case, extraction temperature is preferably 20 to 110° C., more preferably 50 to 90° C., without being limited thereto. In addition, extraction time is preferably 1 to 48 hours, more preferably 2 to 24 hours, without being limited thereto. In addition, the number of extractions is 1 to 5, without being limited thereto.

In the present disclosure, after mixing *Artemisiae capillaris* Herba and *Citrus unshiu* Peel, the extracts of the mixture may be obtained. Alternatively, extracts of each of *Artemisiae capillaris* Herba and *Citrus unshiu* Peel may be obtained and then mixed.

In the present disclosure, after Step 2, the following steps may be additionally performed:

Step 3 of concentrating the filtrate of Step 2 by vacuum evaporation; and

Step 4 of drying the concentrate of Step 3.

In Step 3, vacuum evaporation is preferably performed using a vacuum evaporator or a rotary vacuum evaporator, without being limited thereto. In addition, when drying is performed, reduced-pressure drying, vacuum drying, boiling drying, spray drying, or freeze drying is preferably used, without being limited thereto.

In the present disclosure, after obtaining the *Artemisiae capillaris* Herba and *Citrus unshiu* Peel complex extracts, the complex extracts may be concentrated by vacuum evaporation and dried.

In the present disclosure, after *Artemisiae capillaris* Herba and *Citrus unshiu* Peel are mixed in a weight ratio of 1:0.1 to 5 (i.e., a content of *Artemisiae capillaris* Herba:a content of *Citrus unshiu* Peel=1:0.1 to 5), extraction may be performed to obtain the extracts. Preferably, *Artemisiae capillaris* Herba and *Citrus unshiu* Peel are mixed in a weight ratio of 1:0.3 to 3, more preferably 1:0.5 to 2, most preferably 1:2, and then extraction is performed.

In the present disclosure, the metabolic diseases may include obesity, hyperlipidemia, hypercholesterolemia, diabetes, arteriosclerosis, and fatty liver, preferably obesity, hyperlipidemia, and hypercholesterolemia.

In a specific embodiment of the present disclosure, the present inventors mixed *Artemisiae capillaris* Herba and *Citrus unshiu* Peel in a ratio of 1:0.5 to 2 and obtained the complex extracts of *Artemisiae capillaris* Herba and *Citrus unshiu* Peel.

In addition, the present inventors measured the content of scoparone, which is an ingredient useful for prevention of metabolic diseases including obesity. As a result, it was confirmed that, due to the synergistic effect of *Artemisiae capillaris* Herba and *Citrus unshiu* Peel, the content of scoparone was increased in the *Artemisiae capillaris* Herba and *Citrus unshiu* Peel complex extracts. In addition, when *Artemisiae capillaris* Herba and *Citrus unshiu* Peel were mixed in a ratio of 1:1, the content of scoparone was the highest. Thus, it was confirmed that the synergistic effect of *Artemisiae capillaris* Herba and *Citrus unshiu* Peel was excellent at the mixing ratio.

In addition, the present inventors fed the *Artemisiae capillaris* Herba and *Citrus unshiu* Peel complex extracts to a high-fat diet mouse model for 12 weeks using an oral administration method. Thereafter, change in the levels of cholesterol and triglycerides in the blood was measured. As a result, it was confirmed that the contents of total cholesterol, triglycerides, and LDL in the blood were reduced in an experimental group administered the complex extracts compared to a comparison group not administered the complex extracts.

Thus, in the *Artemisiae capillaris* Herba and *Citrus unshiu* Peel complex extracts according to the present disclosure, the content of scoparone is much higher than in extracts obtained only from *Artemisiae capillaris* Herba. In addition, when a high-fat diet mouse model is administered the complex extracts, the levels of total cholesterol, LDL, and triglycerides in the blood are reduced. Accordingly, the complex extracts of the present disclosure may be used as the active ingredients of a pharmaceutical composition for preventing or treating metabolic diseases including obesity, hyperlipidemia, and hypercholesterolemia.

The pharmaceutical composition according to the present disclosure may further include carriers, excipients, and diluents conventionally used in preparation of pharmaceutical compositions.

The pharmaceutical composition according to the present disclosure may be administered orally or parenterally. For parenteral administration, the complex extracts may be applied to the skin, or may be administered to the body using an injection method such as intraperitoneal injection, rectal injection, subcutaneous injection, intravenous injection, intramuscular injection, or intrathoracic injection, without being limited thereto.

The pharmaceutical composition according to the present disclosure may be prepared in oral formulations such as powders, granules, tablets, capsules, suspensions, emulsions, syrups, and aerosols, externals, suppositories, or sterile injection solutions according to conventional methods. The carriers, excipients, and diluents that may be included in the composition of the present disclosure may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil. When formulated, diluents or excipients such as fillers, extenders, binders, wetting agents, disintegrating agents, and surfactants may be added. Solid formulations for oral administration may include tablets, pills, powders, granules, capsules, and the like. Such solid formulations may be prepared by mixing a mixed herbal medicine with one or more excipients, e.g., starch, calcium carbonate, sucrose, lactose, and gelatin. In addition to excipients, lubricants such as magnesium stearate and talc may be used. Liquid formulations for oral administration may include suspensions, liquids for internal use, emulsions, syrups, and the like. In addition to general diluents such as water and liquid paraffin, various excipients, e.g., wetting agents, sweetening agents, fragrances, preservatives, and the like, may be added to the liquid formulations. Formulations for parenteral administration may include sterile aqueous solutions, non-aqueous solvents, suspensions, emulsions, lyophilized formulations, and suppositories. As the non-aqueous solvents and suspensions, propylene glycol, polyethylene glycol, vegetable oil such as olive oil, injectable esters such as ethyl oleate, and the like may be used. As the bases of suppositories, Witepsol, Macrogol, Tween 61, cacao butter, laurinum, glycerogelatin, and the like may be used.

The preferred dosage of the pharmaceutical composition according to the present disclosure depends on the condition and weight of a patient, the severity of a disease, the form of a drug, and the route and duration of administration, but may be appropriately determined by those skilled in the art. However, to achieve a desired effect, the composition is preferably administrated at a dose of 0.00001 to 1 g/kg per day, more preferably 0.001 to 200 mg/kg per day, most preferably 0.01 to 100 mg/kg per day, without being limited thereto. The dosage may be administered once a day or may be administered several times a day. The dosage does not limit the scope of the invention in any aspect.

In addition, the present disclosure provides a functional health food for preventing or alleviating metabolic diseases, the functional health food containing *Artemisiae capillaris* Herba and *Citrus unshiu* Peel complex extracts as active ingredients.

The description of the *Artemisiae capillaris* Herba and *Citrus unshiu* Peel complex extracts, the mixing ratios thereof, extraction methods, and metabolic diseases are the same as that of the composition for preventing or treating metabolic diseases, and thus repeated description will be omitted. Hereinafter, only the unique composition of the functional health food will be described.

Meanwhile, in the *Artemisiae capillaris* Herba and *Citrus unshiu* Peel complex extracts according to the present disclosure, the content of scoparone is much higher than in extracts obtained only from *Artemisiae capillaris* Herba. In addition, when a high-fat diet mouse model is administered the complex extracts, the levels of total cholesterol, LDL, and triglycerides in the blood are reduced. Accordingly, the complex extracts of the present disclosure may be used as the active ingredients of a functional health food for preventing or treating metabolic diseases including obesity, hyperlipidemia, and hypercholesterolemia.

The functional health food of the present disclosure may be the complex extracts itself or may be prepared by mixing the complex extracts and other food or food ingredients. In addition, the functional health food may be appropriately used according to conventional methods.

Any kind of food may be used as the food without limitation. Examples of the food include drinks, meat, sausage, bread, biscuits, rice cakes, chocolate, candies, snacks, confectionery, pizza, ramen, noodles, gums, dairy products including ice creams, soups, beverages, alcoholic beverages, and vitamin complex. In addition, the food includes all healthy foods in the general sense.

The mixing amount of the complex extracts according to the present disclosure may be appropriately determined according to a purpose of use (prevention or alleviation). In general, the amount of the complex extracts contained in a health food may be 0.01 to 15% by weight based on the total weight of the health food. On the other hand, when ingesting a health food for a long time to improve health or hygiene, the amount of the complex extracts may be less than the above range. In addition, since there is no problem in terms of safety, active ingredients may be used in an amount above the range.

A functional healthy beverage composition of the present disclosure contains the complex extracts as essential ingredients in a predetermined ratio, and may additionally contain various flavors, natural carbohydrates, or the like, without special limitation, as conventional beverages. Examples of the above-mentioned natural carbohydrates include monosaccharides such as glucose and fructose; disaccharides such as maltose and sucrose; and polysaccharides such as conventional sugars including dextrin and cyclodextrin and sugar alcohols including xylitol, sorbitol, and erythritol. As flavoring agents other than those mentioned above, natural flavoring agents, such as thaumatin and stevia extracts (e.g., rebaudioside A, glycyrrhizin, etc.), and synthetic flavoring agents, such as saccharin and aspartame, may be advantageously used.

In addition, the food of the present disclosure may contain various nutrients, vitamins, minerals (electrolytes), flavors including synthetic and natural flavors, coloring agents and flavor enhancers (in the case of cheese and chocolate), pectic acid and salts thereof, alginic acid and salts thereof, organic acids, protective colloidal thickeners, pH adjusters, stabilizers, preservatives, glycerin, alcohols, carbonation agents used in carbonated drinks, and the like. In addition, the composite extracts of the present disclosure may contain flesh added to natural fruit juice, fruit juice beverages, and vegetable beverages. These components may be used independently or in combination. The content of such additives is not so important, but in general, is determined within 0 to about 20 parts by weight based on 100 parts by weight of the complex extracts of the present disclosure.

Hereinafter, the present disclosure will be described in detail with reference to Examples, Experimental Examples, and Preparation Examples.

However, Examples, Experimental Examples, and Preparation Examples below are merely illustrative of the present disclosure, and the content of the present disclosure is not limited thereto.

<Example 1> Preparation of *Artemisiae capillaris* Herba and *Citrus unshiu* Peel Complex Extracts

*Artemisiae capillaris* Herba and *Citrus unshiu* Peel purchased from the Kwang Myung Dang pharmaceutical company were added to a solvent consisting of 2,000 mL of distilled water and 2,000 mL of 83% ethanol according to the compositions shown in Table 1, and extraction was performed at 70° C. for 3 hours to obtain a filtrate. Then, vacuum evaporation and freeze drying were performed on the obtained filtrate using a rotary evaporator (Rotavapor R-100, BUCH Co.) to obtain *Artemisiae capillaris* Herba and *Citrus unshiu* Peel complex extracts.

TABLE 1

|  | Conditions | Examples | | | | | |
| --- | --- | --- | --- | --- | --- | --- | --- |
|  |  | 1-1 | 1-2 | 1-3 | 1-4 | 1-5 | 1-6 |
| Mixture composition | *Artemisiae capillaris* Herba (g) | 500 | 500 | 500 | 500 | 500 | 0 |
|  | *Citrus unshiu* Peel (g) | 0 | 250 | 500 | 750 | 1,000 | 1,000 |
| Solvent composition | Distilled water (mL) | 2,000 | 2,000 | 2,000 | 2,000 | 2,000 | 2,000 |
|  | 83% ethanol (mL) | 2,000 | 2,000 | 2,000 | 2,000 | 2,000 | 2,000 |
| Extraction temperature (° C.) |  | 70 | 70 | 70 | 70 | 70 | 70 |
| Extraction time (hour) |  | 3 | 3 | 3 | 3 | 3 | 3 |

<Experimental Example 1> Analysis of Content of Scoparone Contained in *Artemisiae capillaris* Herba and *Citrus unshiu* Peel Complex Extracts Scoparone has effects of inhibiting adipocyte differentiation and inhibiting accumulation of triglycerides in adipocytes, and has been well known as a useful compound for preventing metabolic diseases including obesity (Jung-Ran Noh et al., 2013). Thus, to determine the effect of *Artemisiae capillaris* Herba and *Citrus unshiu* Peel complex extracts on treatment of metabolic diseases including obesity, the content of scoparone contained in the extracts prepared in Example 1 was analyzed using an LC-mass spectrometer.

TABLE 2

|  | Examples | | | | | |
| --- | --- | --- | --- | --- | --- | --- |
|  | 1-1 | 1-2 | 1-3 | 1-4 | 1-5 | 1-6 |
| Concentration (μg/mL) | 68.2792 | 74.0251 | 83.7753 | 76.4366 | 76.3629 | 0 |
| Content (mg/g) | 6.8279 | 7.4025 | 8.3775 | 7.6437 | 7.6363 | 0 |

As a result, as shown in Table 2, for Example 1-6 in which extracts obtained only from *Citrus unshiu* Peel are used, scoparone is not included. In addition, for Example 1-1 in which extracts obtained only from *Artemisiae capillaris* Herba are used, scoparone is included. However, the content of scoparone in Example 1-1 is less than in Examples 1-2 to 1-5 in which complex extracts obtained from *Artemisiae capillaris* Herba and *Citrus unshiu* Peel mixed in a ratio of 1:0.5 to 2 are used. In addition, for Example 1-3 in which complex extracts obtained from *Artemisiae capillaris* Herba and *Citrus unshiu* Peel mixed in a ratio of 1:1 are used, the content of scoparone is the highest.

Based on the above results, it can be seen that, compared to extracting *Artemisiae capillaris* Herba alone, when extraction is performed after mixing *Artemisiae capillaris* Herba and *Citrus unshiu* Peel, the content of scoparone is significantly increased due to the synergistic effect of these two substances. Accordingly, it can be confirmed that, compared to extracts obtained only from *Artemisiae capillaris* Herba, therapeutic effect on metabolic diseases including obesity is increased. In addition, it can be confirmed that, when *Artemisiae capillaris* Herba and *Citrus unshiu* Peel are mixed in a ratio of 1:0.5 to 2, the therapeutic effect of the *Artemisiae capillaris* Herba and *Citrus unshiu* Peel complex extracts is further improved.

<Experimental Example 2> Evaluation of Therapeutic Effect of *Artemisiae capillaris* Herba and *Citrus unshiu* Peel Complex Extracts on Hyperlipidemia and Hypercholesterolemia <2-1> Experimental Animal Production 64 six-week-old female ICR mice were purchased from SLC Co. and acclimated for one week under breeding conditions of a temperature range of 22±1° C., a humidity range of 41±1%, and a 12-hour light/12-hour dark cycle. During this period, the mice were fed a normal diet. Then, the mice were randomly divided into 16 and 48 individuals. To adapt the mice to feed, the 16 individuals (a normal diet-fed group) were fed a normal diet (CA.170481, Teklad Co.) and the 48 individuals (a high-fat diet-fed group) were fed a high-fat diet (D12451, Research Diets Co.) containing 45 kcal % fat under the same breeding conditions as above for one week.

After a total of 14 days of adaptation, 32 healthy mice were selected and divided into experimental groups shown in Table 3 below. Specifically, eight mice were selected from the normal diet-fed group and assigned to a normal diet group. 24 mice were selected from the high-fat diet-fed group, eight of which were assigned to a high-fat diet group, a high-fat diet+complex extracts administration group, and a high-fat diet+Lovastatin administration group, respectively. Each experimental group was orally administered distilled water or the *Artemisiae capillaris* Herba and *Citrus unshiu* Peel complex extracts of Examples 1-3 containing the highest content of scoparone once a day for 12 weeks. In addition, a comparison group was orally administered Lovastatin (Hanmi Pharm. Co., Ltd), which is used to treat hyperlipidemia and hypercholesterolemia, once a day for 12 weeks. In this case, the complex extracts and Lovastatin were each suspended in distilled water and administered orally. In addition, the normal group was fed a normal diet and other experimental groups were fed a high-fat diet for 12 weeks.

TABLE 3

| Experimental groups | Administered samples | Diet |
| --- | --- | --- |
| Normal group | Oral administration of distilled water once a day for 12 weeks | Normal diet |
| High-fat diet group | Oral administration of distilled water once a day for 12 weeks | High-fat diet containing 45 kcal % fat |
| High-fat diet + complex extracts administration group | Oral administration of 100 mg of *Artemisiae capillaris* Herba and *Citrus unshiu* Peel complex extracts of Example 1-3/10 ml of distilled water/kg/day for 12 weeks | High-fat diet containing 45 kcal % fat |
| High-fat diet + Lovastatin administration group | Oral administration of 20 mg of Lovastatin/ 10 mL of distilled water/ kg/day for 12 weeks | High-fat diet containing 45 kcal % fat |

<2-2> Evaluation of Therapeutic Effect of *Artemisiae capillaris* Herba and *Citrus unshiu* Peel Complex Extracts on Hyperlipidemia and Hypercholesterolemia In the experimental groups of Experimental Example <2-1>, changes in the contents of triglycerides and cholesterol were confirmed.

Specifically, each experimental group of Experimental Example <2-1> was orally administered samples for 12 weeks. On the last day of the experiment, all animals were bled under ether inhalation anesthesia, and 1 mL of the collected blood was centrifuged for 10 minutes at 3,000 rpm to isolate plasma. The contents of total cholesterol, triglycerides, and low density lipoprotein cholesterol (LDL) in the isolated plasma were measured using an Analyst III kit (Hemagen Diagnositics Co.) according to a manufacturer's procedure, and the content of high density lipoprotein cholesterol (HDL) was measured using an AU400 kit (Olympus Co.) according to a manufacturer's procedure.

TABLE 4

| | Serum content (mg/dl) | | | |
| --- | --- | --- | --- | --- |
| Experimental groups | Total cholesterol | Triglycerides | LDL | HDL |
| Normal group | 65.29 ± 1.91 | 51.26 ± 2.07 | 9.93 ± 1.23 | 69.95 ± 2.60 |
| High-fat diet group | 151.69 ± 6.86 | 129.27 ± 9.13 | 18.57 ± 0.52 | 46.52 ± 3.39 |
| High-fat diet + complex extracts administration group | 93.36 ± 4.41 | 57.35 ± 3.41 | 12.89 ± 0.61 | 69.86 ± 1.69 |
| High-fat diet + Lovastatin administration group | 83.26 ± 7.40 | 81.43 ± 5.24 | 14.91 ± 0.46 | 62.44 ± 1.96 |

As a result, as shown in Table 4, it can be seen that the contents of total cholesterol, triglycerides, and LDL are highest in the high-fat diet group. On the other hand, it can be seen that the contents of total cholesterol, triglycerides, and LDL are significantly reduced in the high-fat diet+complex extracts administration group. In particular, it can be seen that, in the high-fat diet+complex extracts administration group, the contents of triglycerides and LDL are further reduced compared to the high-fat diet+Lovastatin administration group. On the other hand, the HDL content of the high-fat diet+complex extracts administration group is similar to that of the normal group.

Based on these results, the *Artemisiae capillaris* Herba and *Citrus unshiu* Peel complex extracts were found to be effective in treating metabolic diseases such as hyperlipidemia and hypercholesterolemia due to increased cholesterol in the blood by reducing the levels of total cholesterol, LDL, and triglycerides without affecting the level of HDL.

Preparation Examples for the composition of the present disclosure are described below.

<Preparation Example 1> Preparation of Pharmaceutical Formulations Containing Complex Extracts of the Present Disclosure as Active Ingredients <1-1> Preparation of Powder
Complex extracts of the present disclosure: 10 mg
Lactose: 1 g
The above ingredients were mixed, and then a sealable bag was filled with the ingredients to prepare powder.

<1-2> Preparation of Tablets
Complex extracts of the present disclosure: 0.1 mg
Corn starch: 100 mg
Lactose: 100 mg
Magnesium stearate: 2 mg
The above ingredients were mixed, and then tableting was performed according to a conventional method for preparing tablets to prepare tablets.

<1-3> Preparation of Capsules
Complex extracts of the present disclosure: 0.1 mg
Corn starch: 100 mg
Lactose: 100 mg
Magnesium stearate: 2 mg
The above ingredients were mixed, and then gelatin capsules were filled with the ingredients according to a conventional method for preparing capsules to prepare capsules.

<1-4> Preparation of Pills
Complex extracts of the present disclosure: 1 mg
Lactose: 1.5 g
Glycerin: 1 g
Xylitol: 0.5 g
The above ingredients were mixed, and then pills were prepared to be 4 g per pill according to a conventional method.

<1-5> Preparation of Granules
Complex extracts of the present disclosure: 0.15 mg
Soybean extracts: 50 mg
Glucose: 200 mg
Starch: 600 mg
The above ingredients were mixed, 100 mg of 30% ethanol was added thereto, drying was performed at 60° C. to form granules, and then powder paper was filled with the granules.

<Preparation Example 2> Preparation of Health Food Containing Complex Extracts of the Present Disclosure as Active Ingredients <2-1> Preparation of Flour Food
0.5 to 5.0 parts by weight of the complex extracts of the present disclosure was added to flour, and the mixture was used to prepare bread, cakes, cookies, crackers, and noodles.

<2-2> Preparation of Soup and Gravies
0.1 to 5.0 parts by weight of the complex extracts of the present disclosure was added to soup and gravies to prepare meat products, noodle soup, and gravies for health promotion.

<2-3> Preparation of Ground Beef
10 parts by weight of the complex extracts of the present disclosure was added to ground beef to prepare to ground beef for health promotion.

<2-4> Preparation of Dairy Products
5 to 10 parts by weight of the complex extracts of the present disclosure was added to milk, and various dairy products, such as butter and ice cream, were prepared using the milk.

<2-5> Preparation of Roasted Grain Powder
Brown rice, barley, glutinous rice, and adlay were gelatinized and dried according to a known method, roasted, and then powder having a particle size of 60 mesh was prepared using a grinder.

Black bean, black sesame, and perilla were steamed and dried according to a known method, roasted, and then powder having a particle size of 60 mesh was prepared using a grinder.

The complex extracts of the present disclosure were concentrated using a vacuum evaporator, dried using a spray-hot air dryer to obtain a dried product, and then the dried product was ground using a grinder to prepare powder having a particle size of 60 mesh.

The grains, seeds, and the composite extracts of the present disclosure prepared above were blended according to the following ratio.

Grains (30 parts by weight of unpolished rice, 15 parts by weight of adlay, 20 parts by weight of barley),
Seeds (7 parts by weight of perilla, 8 parts by weight of black bean, 7 parts by weight of black sesame),
Complex extracts of the present disclosure (3 parts by weight),
*Ganoderma lucidum* (0.5 parts by weight), and
*Rehmannia* root (0.5 parts by weight)

<Preparation Example 3> Preparation of Healthy Drink Containing Complex Extracts of the Present Disclosure as Active Ingredients <3-1> Preparation of Healthy Drink
High fructose corn syrup (0.5%), oligosaccharides (2%), sugar (2%), salt (0.5%), water (75%), and 100 mL of the complex extracts of the present disclosure were homogeneously mixed, instant sterilization was performed, and the mixture was placed in small containers such as glass bottles and plastic bottles.

<3-2> Preparation of Vegetable Juice
100 ml of the complex extracts of the present disclosure was added to 1,000 ml of tomato juice or carrot juice to prepare vegetable juice.

<3-3> Preparation of Fruit Juice
100 ml of the complex extracts of the present disclosure was added to 1,000 ml of apple juice or grape juice to prepare fruit juice.

In the *Artemisiae capillaris* Herba and *Citrus unshiu* Peel complex extracts according to the present disclosure, the content of ingredients useful for prevention of metabolic diseases including obesity is much higher than in extracts obtained only from *Artemisiae capillaris* Herba. In addition, when a high-fat diet mouse model is administered the complex extracts, the levels of total cholesterol, LDL, and triglycerides in the blood are reduced. Accordingly, the complex extracts of the present disclosure can be used as a composition or functional material for preventing or treating metabolic diseases including obesity, hyperlipidemia, and hypercholesterolemia.

What is claimed is:

1. A pharmaceutical composition for treating metabolic diseases, the pharmaceutical composition containing *Artemisiae capillaris* Herba and *Citrus unshiu* Peel complex extracts as active ingredients,
    wherein after *Artemisiae capillaris* Herba and *Citrus unshiu* Peel are mixed in a weight ratio of 1:0.5 to 1:2, an extraction is performed to obtain the *Artemisiae capillaris* ..Herba and *Citrus unshiu* Peel complex extracts, and
    wherein the extraction is performed at a temperature of 50 to 70° C. using water, a lower alcohol having 1 to 2 carbon atoms, or a mixture thereof as a solvent.

2. The pharmaceutical composition according to claim 1, wherein the metabolic diseases are one or more selected from the group consisting of obesity, hyperlipidemia, hypercholesterolemia, diabetes, arteriosclerosis, and fatty liver.

3. A functional health food for alleviating metabolic diseases, the functional health food containing *Artemisiae capillaris* Herba and *Citrus unshiu* Peel complex extracts as active ingredients,
    wherein after *Artemisiae capillaris* Herba and *Citrus unshiu* Peel are mixed in a weight ratio of 1:0.5 to 1:2, an extraction is performed to obtain the *Artemisiae capillaris* Herba and *Citrus unshiu* Peel complex extracts, and
    wherein the extraction is performed at a temperature of 50 to 70° C. using water, a lower alcohol having 1 to 2 carbon atoms, or a mixture thereof as a solvent.

4. The functional health food according to claim 3, wherein the metabolic diseases are one or more selected from the group consisting of obesity, hyperlipidemia, hypercholesterolemia, diabetes, arteriosclerosis, and fatty liver.

* * * * *